(12) United States Patent
Ye et al.

(10) Patent No.: US 12,280,221 B2
(45) Date of Patent: Apr. 22, 2025

(54) SURGICAL INSTRUMENT THAT ENABLES ACCESS TO A REGION OF INTEREST

(71) Applicant: The Johns Hopkins University, Baltimore, MD (US)

(72) Inventors: Jack Ye, East Elmhurst, NY (US); Kevin Tu, Baltimore, MD (US); Rohith Bhethanabotla, San Jose, CA (US); Jody Mou, Toronto (CA); Sun Jay Yoo, Baltimore, MD (US); Alan R. Cohen, Owings Mills, MD (US); Rajiv Iyer, Baltimore, MD (US); Daniel Rosenthal Garber, Baltimore, MD (US); Callie Deng, Gaithersburg, MD (US); Linh Tran, Baltimore, MD (US); Wataru Ishida, Baltimore, MD (US); Mark Elliot Shifman, Jersey City, NJ (US); Ananyaa Sivakumar, Baltimore, MD (US); Rene Debrabander, Towson, MD (US); Reena Elizebath, Glen Mills, PA (US)

(73) Assignee: The Johns Hopkins University, Baltimore, MD (US)

( * ) Notice: Subject to any disclaimer, the term of this patent is extended or adjusted under 35 U.S.C. 154(b) by 743 days.

(21) Appl. No.: 17/310,721

(22) PCT Filed: Feb. 21, 2020

(86) PCT No.: PCT/US2020/019293
§ 371 (c)(1),
(2) Date: Aug. 19, 2021

(87) PCT Pub. No.: WO2020/172573
PCT Pub. Date: Aug. 27, 2020

(65) Prior Publication Data
US 2022/0176070 A1  Jun. 9, 2022

Related U.S. Application Data

(60) Provisional application No. 62/809,438, filed on Feb. 22, 2019.

(51) Int. Cl.
*A61M 25/10* (2013.01)
*A61B 34/20* (2016.01)
(Continued)

(52) U.S. Cl.
CPC ......... *A61M 25/0026* (2013.01); *A61B 34/20* (2016.02); *A61B 90/10* (2016.02);
(Continued)

(58) Field of Classification Search
CPC ...... A61M 25/0026; A61M 2039/0235; A61M 25/007; A61M 25/10; A61B 2017/3445;
(Continued)

(56) References Cited

U.S. PATENT DOCUMENTS 6,537,194 B1 * 3/2003 Winkler ............... A61N 5/1002
600/3
6,537,232 B1 * 3/2003 Kucharczyk ....... G01R 33/5601
600/561

(Continued)

FOREIGN PATENT DOCUMENTS

EP 1142532 A2 10/2001

OTHER PUBLICATIONS

International Search Report and Written Opinion—PCT/US2020/019293—ISA/RU—May 25, 2020.

*Primary Examiner* — Deanna K Hall
(74) *Attorney, Agent, or Firm* — Harrity & Harrity, LLP

(57) ABSTRACT

A surgical instrument may include a multi-lumen catheter configured to be inserted within the tissue. The multi-lumen catheter may include a first lumen that may enable a flow of a fluid, a second lumen that may receive a navigation probe
(Continued)

that may facilitate an ability to locate the region of interest within the tissue, and an expandable membrane that may be situated toward a distal end of the first lumen to form an expandable cavity. The expandable cavity may be configured to expand or contract based on the flow of the fluid through the first lumen. The surgical instrument may include a fluid line, coupled to the first lumen, that may supply the fluid to the first lumen to enable the expandable cavity to expand or withdraw the fluid from the first lumen to enable the expandable cavity to contract.

41 Claims, 12 Drawing Sheets

(51) Int. Cl.
*A61B 90/10* (2016.01)
*A61M 25/00* (2006.01)
*A61M 39/02* (2006.01)
*A61B 17/00* (2006.01)
*A61B 17/02* (2006.01)

(52) U.S. Cl.
CPC .......... *A61M 25/007* (2013.01); *A61M 25/10* (2013.01); *A61M 39/0208* (2013.01); *A61B 2017/00477* (2013.01); *A61B 2017/00557* (2013.01); *A61B 2017/0225* (2013.01); *A61B 2034/2055* (2016.02); *A61B 2034/2065* (2016.02); *A61M 2039/0232* (2013.01); *A61M 2039/0235* (2013.01)

(58) Field of Classification Search
CPC .. A61B 2034/2055; A61B 2017/00557; A61B 34/20
See application file for complete search history.

(56) References Cited

U.S. PATENT DOCUMENTS

2009/0062872 A1\* 3/2009 Chin .................. A61B 1/00082
606/86 R
2016/0175575 A1 6/2016 Tallarida et al.
2017/0319831 A1 11/2017 Gill \* cited by examiner Cross-sectional View Navigation Probe Removal

330

Surgical Sheath Insertion

340

Slides over expandable membrane

Multi-lumen Catheter Removal

350
Integration with Snake Arm

Port of Entry Access

360

Suction

Bayoneted Surgical Tools

SURGICAL INSTRUMENT THAT ENABLES ACCESS TO A REGION OF INTEREST

RELATED APPLICATIONS

This application is a 371 national stage of PCT Application PCT/US2020/019293 filed on Feb. 21, 2020, entitled "SURGICAL INSTRUMENT THAT ENABLES ACCESS TO A REGION OF INTEREST," which claims priority to U.S. Provisional Patent Application No. 62/809,438, filed on Feb. 22, 2019, both of which are hereby expressly incorporated by reference herein.

BACKGROUND

For a patient with a suspicious lesion, such as a brain tumor, primary treatment involves removal of the suspicious lesion. In some instances, the suspicious lesion may be in a region of interest that is below the surface of tissue of an organ. Accordingly, to access the region of interest, an incision may be made in the tissue, so that a surgeon can access the lesion via through the incision.

SUMMARY

According to some implementations, a surgical instrument to enable access to a region of interest within a tissue may include: a multi-lumen catheter configured to be inserted within the tissue, the multi-lumen catheter comprising: a first lumen configured to enable a flow of a fluid, a second lumen configured to receive a navigation probe that facilitates location of the region of interest within the tissue, and an expandable membrane situated toward a distal end of the first lumen to form an expandable cavity, wherein the expandable cavity is configured to expand or contract based on the flow of the fluid through the first lumen; and a fluid line, coupled to the first lumen, that is configured to: supply the fluid to the first lumen to enable the expandable cavity to expand, or withdraw the fluid from the first lumen to enable the expandable cavity to contract.

According to some implementations, a surgical instrument system may include a navigation probe that enables a region of interest to be located within a tissue; a multi-lumen catheter configured to receive the navigation probe, wherein the multi-lumen catheter comprises: a first lumen configured to enable a flow of a fluid, a second lumen configured to receive the navigation probe, and an expandable membrane situated toward a distal end of the first lumen to form an expandable cavity, wherein the expandable cavity is configured to expand or contract based on the flow of the fluid through the first lumen; a fluid line, coupled to the first lumen, that is configured to: supply the fluid to the first lumen to enable the expandable cavity to expand, or withdraw the fluid from the first lumen to enable the expandable cavity to contract; and a surgical sheath configured to be received within the tissue when the expandable cavity is expanded, wherein the expandable membrane, when the expandable cavity is expanded and the surgical sheath is received within the tissue, is received within the surgical sheath.

According to some implementations, a surgical procedure associated with accessing a region of interest may include creating an incision in a tissue; inserting a multi-lumen catheter with a navigation probe in the incision in the tissue, wherein the multi-lumen catheter comprises: a first lumen configured to enable a flow of a fluid, a second lumen configured to receive the navigation probe, and an expandable membrane situated to form an expandable cavity based on the flow of the fluid; locating the region of interest using the navigation probe; supplying, via the first lumen, the fluid to the expandable cavity, wherein the fluid is supplied to the expandable cavity to cause the expandable membrane to apply a relatively uniform force against the tissue of the incision; inserting a surgical sheath within the incision and over the expandable membrane; withdrawing the fluid from the expandable cavity; and removing the multi-lumen catheter from the surgical sheath to create a corridor of access, through the surgical sheath, to the region of interest.

According to some implementations, a surgical instrument system may include a navigation probe that enables a region of interest to be located within a tissue; a multi-lumen catheter configured to receive the navigation probe, wherein the multi-lumen catheter comprises: a first lumen configured to enable a flow of a fluid, a second lumen configured to receive the navigation probe, and a first expandable membrane situated toward a distal end of the first lumen to form a first expandable cavity, wherein the first expandable cavity is configured to expand or contract based on the flow of the first fluid through the first lumen; a primary fluid line, coupled to the first lumen, that is configured to: supply the first fluid to the first lumen to enable the first expandable cavity to expand, or withdraw the first fluid from the first lumen to enable the first expandable cavity to contract; and a second expandable membrane to form a first expandable cavity, wherein the second expandable membrane is coaxial to the first expandable membrane at the distal end of the first lumen, and wherein the second expandable cavity is configured to expand or contract based on a flow of second fluid to or from the second expandable cavity; a secondary fluid line, coupled to the second expandable cavity, that is configured to: supply the second fluid to the second expandable cavity to cause the second expandable cavity to expand, or withdraw the second fluid from the first lumen to enable the second expandable cavity to contract; and a surgical sheath configured to be received within a tubular structure formed by the second expandable cavity when the second expandable cavity is expanded, wherein the surgical sheath is configured to form a corridor of access to the region of interest.

According to some implementations, a surgical procedure associated with accessing a region of interest may include creating an incision in a tissue; inserting a surgical instrument with a navigation probe in the incision in the tissue, wherein the surgical instrument comprises: a multi-lumen catheter that includes: a first lumen configured to enable a flow of first fluid, a second lumen configured to receive the navigation probe, a first expandable membrane situated to form a first expandable cavity based on the first flow of the fluid; and a second expandable membrane situated to form a second expandable cavity based on a flow of a second fluid; locating the region of interest using the navigation probe; supplying, via a primary fluid line coupled to the first lumen, the fluid to the first expandable cavity, wherein the first fluid is supplied to the first expandable cavity to cause the second expandable membrane to apply a relatively uniform force against the tissue of the incision; supplying, via a second fluid line coupled to the second expandable cavity, the second fluid to the second expandable cavity, wherein the second fluid is supplied to the second expandable cavity to cause the second expandable membrane to form a tubular structure that provides a flexible barrier between the tissue and the first expandable cavity; withdrawing the first fluid from the first expandable cavity to reduce friction between the first expandable membrane and the tubular structure formed by the second expandable membrane; removing the multi-lumen catheter from the tubular structure without removing the second expandable membrane from the incision; and inserting a surgical sheath into the tubular structure to create a corridor of access, through the surgical sheath, to the region of interest.

DETAILED DESCRIPTION

Figure 1:
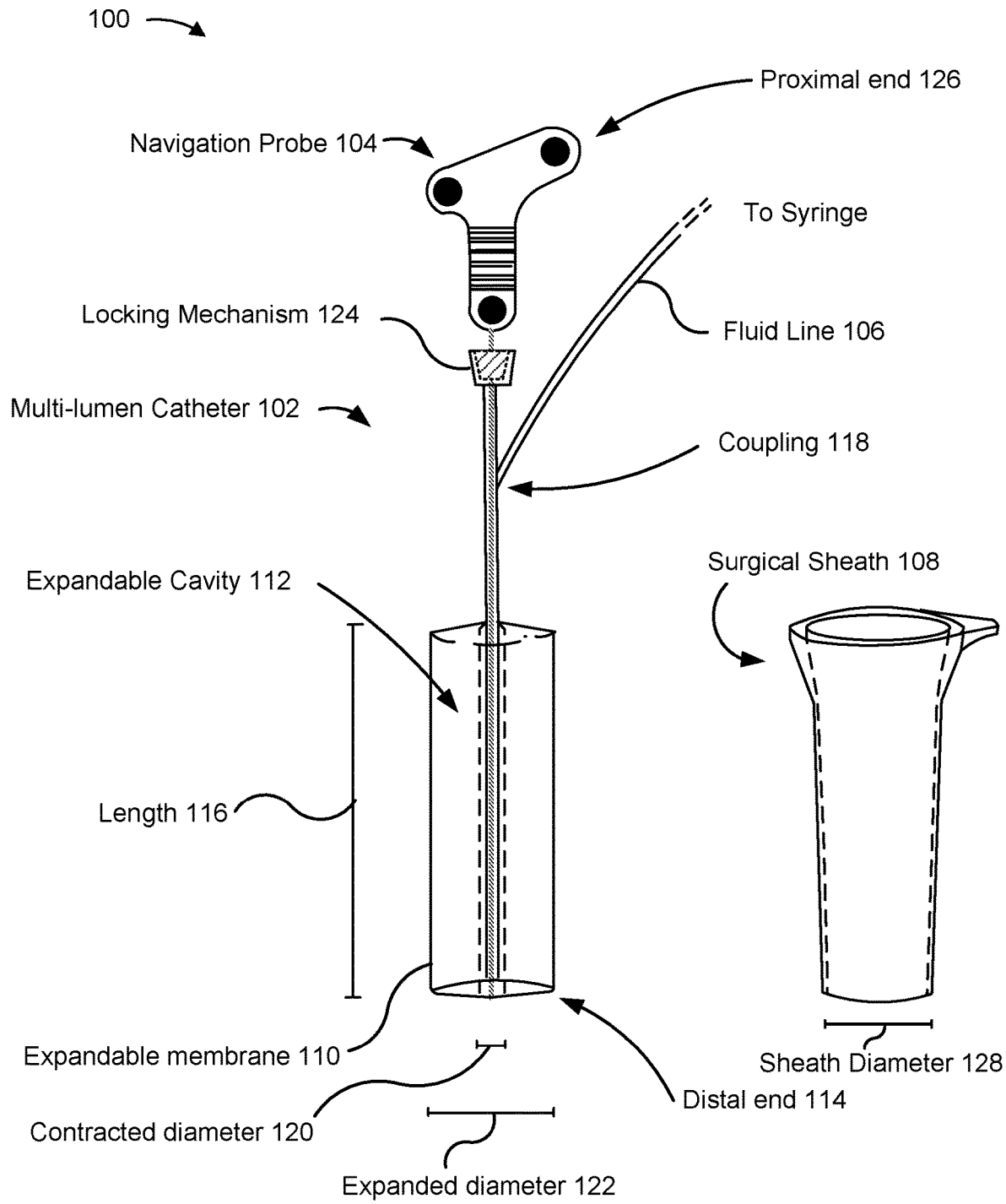
FIG. 1 is a diagram of an example implementation of a surgical instrument system described herein.

The following detailed description of example implementations refers to the accompanying drawings. The same reference numbers in different drawings may identify the same or similar elements.

In many instances, a surgical procedure to access a region of interest of a patient involves creating an incision in tissue and accessing the region of interest via the incision. The region of interest may include a lesion, an aneurysm, and/or any other type of tissue or region of a patient's body that may require corrective or resection procedures. Furthermore, to gain access through the incision, the surgical procedure may include a retraction procedure that opens the incision to create a corridor of access to the region of interest. Previous retraction procedures involve a surgeon using one or more metal blade retractors to displace the tissue. Such metal blade retractors cause substantially disproportionate disturbances to surrounding tissue of the incision (e.g., due to disproportionate amounts of force that are applied to various parts of the tissue by the metal blade retractors). In some cases, a surgeon may use a tubular retractor to more uniformly distribute the force applied on the surrounding tissue of the incision. However, such tubular retractors can still disturb the surrounding tissue during the initial insertion and positioning of the tubular retractors (e.g., because the tubular retractors themselves are used to widen the incision). Further, the greater the diameter of the tubular retractor, the greater the disturbance to the surrounding tissue. When considering that such regions of interest can occur within sensitive tissue of an individual, such as brain tissue, such disturbances to the tissue, caused by metal retractors and/or insertions of tubular retractors, can cause severe, secondary injuries. For example, excessive focal pressure on parts of the brain tissue from the metal blade retractors or tubular retractor insertions can cause brain swelling, hemorrhage, infarction, and/or the like.

Some implementations described herein provide a surgical instrument system that enables improved access to a region of interest within tissue (e.g., brain tissue) of a patient by enabling a relatively uniform force to be applied to the tissue during a retraction procedure. For example, an example surgical instrument system may include a multi-lumen catheter with a navigation probe (e.g., to enable navigation to the region of interest) and one or more expandable cavities formed from one or more expandable membranes to widen the incision. A lumen of the multi-lumen catheter may enable flow of a fluid (e.g., a gas or liquid, such as air, water, saline, and/or the like), to and/or from an expandable cavity to expand or contract one of the expandable membranes. When the expandable cavity is supplied with the fluid, the expandable membrane may apply a relatively uniform force to the tissue that is in contact with the expandable membrane (e.g., the tissue of the incision) to widen the incision. Furthermore, a surgical sheath (e.g., a tubular retractor) can be inserted into the widened incision by being slid over the expandable membrane during insertion. In some implementations, the surgical sheath may be inserted between two expandable cavities used to widen the incision (e.g., to prevent the surgical sheath from coming into direct contact with the tissue). Accordingly, the one or more expandable cavities of the multi-lumen catheter enable application of a relatively uniform force to the tissue of the incision during retraction (e.g., when being supplied or filled with a fluid) and enables the surgical sheath to be inserted without disproportionately disturbing portions of the tissue (e.g., due to the incision being widened before insertion of the surgical sheath and/or by serving as a flexible buffer between the surgical sheath and the tissue when the surgical sheath is inserted between two expandable cavities).

While some implementations described herein may refer to using the surgical instrument system to access a region of interest in brain tissue, the surgical instrument system can be used to access regions of interest within one or more other types of tissue of a patient (e.g., tissue of one or more other organs of the patient).

FIG. 1 is a diagram of an example implementation of a surgical instrument system 100 described herein. Surgical instrument system 100 includes a multi-lumen catheter 102, a navigation probe 104, a fluid line 106, and a surgical sheath 108.

Multi-lumen catheter 102 includes a plurality of lumens (e.g., spaces of the catheter). In some implementations, at least two lumens of the plurality of lumens may be coaxial relative to one another. For example, a first lumen may be coaxial within a second lumen. In such cases, at least one or more of the lumens may be formed from one or more tubal structures (e.g., one or more rigid tubal structures). For example, the one or more lumens may be formed within and/or between the tubal structures. Accordingly, in some implementations, multi-lumen catheter 102 may include a plurality of tubal structures that are coaxial to one another.

Multi-lumen catheter 102 may include an expandable membrane 110. Expandable membrane 110, based on a flow of fluid from fluid line 106 and/or through a fluid lumen of multi-lumen catheter 102, may form an expandable cavity 112 of multi-lumen catheter 102. As shown, expandable membrane 110 is situated around a distal end 114 of multi-lumen catheter 102. Expandable membrane 110 and/or multi-lumen catheter 102 may be configured as a balloon catheter that is configured to widen an incision in tissue to permit access to a region of interest in accordance with a use of surgical instrument system 100, as described herein.

Expandable cavity 112 may be formed to be substantially cylindrical (e.g., when expanded and/or contracted when not inserted within tissue) and have a length 116 (e.g., 5 centimeters (cm), 8 cm, and/or the like). In some implementations, length 116 may correspond to a depth of an incision made in the tissue to access to a region of interest. For example, the length of the expandable membrane 110 may be greater than or equal to a depth of the region of interest in the tissue, such that, when distal end 114 of multi-lumen catheter 102 is inserted into the tissue, an axial surface of expandable membrane 110 may be in contact with the tissue of the incision. Expandable membrane 110 may be circumferentially attached (e.g., at a first circumferential location of multi-lumen catheter 102) at distal end 114 of the multi-lumen catheter 102. Furthermore, expandable membrane 110 may be circumferentially attached between distal end 114 and a coupling 118 of fluid line 106 (e.g., a coupling that connects fluid line 106 to a lumen of multi-lumen catheter 102).

Coupling 118 may enable fluid to flow between a fluid lumen of multi-lumen catheter 102 and fluid line 106. For example, as fluid is supplied from fluid line 106, through the fluid lumen of multi-lumen catheter 102, and into expandable cavity 112, expandable membrane 110 may expand from a contracted diameter 120 (e.g., 5 millimeters (mm) or less) to an expanded diameter 122 (e.g., greater than 1 cm). Additionally, or alternatively, as fluid is withdrawn from expandable cavity 112, into the fluid lumen of multi-lumen catheter 102 and fluid line 106, expandable membrane 110 may contract from the expanded diameter 122 to the contracted diameter 120. The flow of fluid may be controlled via a syringe attached to an end opposite coupling 118. Accordingly, when an individual (e.g., a surgeon, a nurse, and/or the like) interacts with the syringe, the fluid may be supplied to and/or withdrawn from expandable cavity 112.

Navigation probe 104 may be any suitable navigation probe that facilitates an ability (e.g., an ability of a surgeon) to locate and/or navigate to a region of interest within tissue. For example, navigation probe 104 may include a neuro-navigation probe that permits access to a region of interest in a brain of a patient. In some implementations, navigation probe 104 is associated with a digital image processing system that permits a surgeon navigate to the region of interest via a digital image display. As shown in FIG. 1, the navigation probe 104 of the example surgical instrument system 100 may be received within a probe lumen of multi-lumen catheter 102. In some implementations, the probe lumen may be an innermost coaxial lumen of the multi-lumen catheter 102. In such cases, the probe lumen may be coaxially within a fluid lumen of multi-lumen catheter 102.

Navigation probe 104 may be attached to multi-lumen catheter 102 using a locking mechanism 124 (e.g., a Heparin lock, a twist lock (e.g., a threaded locking mechanism), and/or the like). Accordingly, navigation probe 104 may be received within multi-lumen catheter 102, attached to multi-lumen catheter 102 via locking mechanism 124, such that movement of the navigation probe 104 corresponds to movement of multi-lumen catheter 102. In other words, when navigation probe 104 is attached to multi-lumen catheter 102, if a surgeon moves navigation probe 104 (e.g., while attempting to navigate to a region of interest), multi-lumen catheter 102 may correspondingly move. Additionally, or alternatively, distal end 114 may substantially align (e.g., within a manufacturing tolerance) with an end of the navigation probe. Locking mechanism 124 may be situated toward a proximal end 126 of multi-lumen catheter 102. Proximal end 126 of multi-lumen catheter 102 is configured to be utilized by a surgeon during a retraction procedure involving surgical instrument system 100 while distal end 114 is inserted within the tissue. For example, the surgeon may hold a handle of navigation probe 104 that is situated at or toward proximal end 126, navigate navigation probe 104 (and correspondingly multi-lumen catheter 102) to the region of interest via the handle, and hold navigation probe 104 in place to allow insertion of surgical sheath 108 into the incision and over expandable membrane 110. In some implementations, navigation probe 104 may remain within multi-lumen catheter 102 until after expansion to ensure optimal navigation to the region of interest and that the multi-lumen catheter remains over or near the region of interest during expansion.

Surgical sheath 108 has a sheath diameter 128 that may correspond to expanded diameter 122. For example, sheath diameter 128 may be less than or equal to expanded diameter 122. Accordingly, when surgical sheath 108 is inserted within the incision, while expandable cavity 112 is supplied with fluid, expandable membrane 110 may be tightly and flexibly received within surgical sheath 108. In this way, as described herein, the widened incision may transition from being widened by expandable membrane 110 to held open by surgical sheath 108. After surgical sheath 108 is inserted into the incision of the tissue, multi-lumen catheter 102 (including navigation probe 104) may be removed from surgical sheath 108, leaving a corridor of access to the region of interest. Prior to removal of multi-lumen catheter 102, expandable cavity 112 may be contracted by withdrawing fluid from expandable cavity 112, through the fluid lumen of multi-lumen catheter 102, and into fluid line 106.

In some implementations, surgical sheath 108 may be configured for use with a mechanical arm (or a snake arm) and/or one or more other implements to permit the insertion of the surgical sheath 108 within the tissue.

As indicated above, FIG. 1 is provided merely as one or more examples. Other examples may differ from what is described with regard to FIG. 1.

Figure 2A:
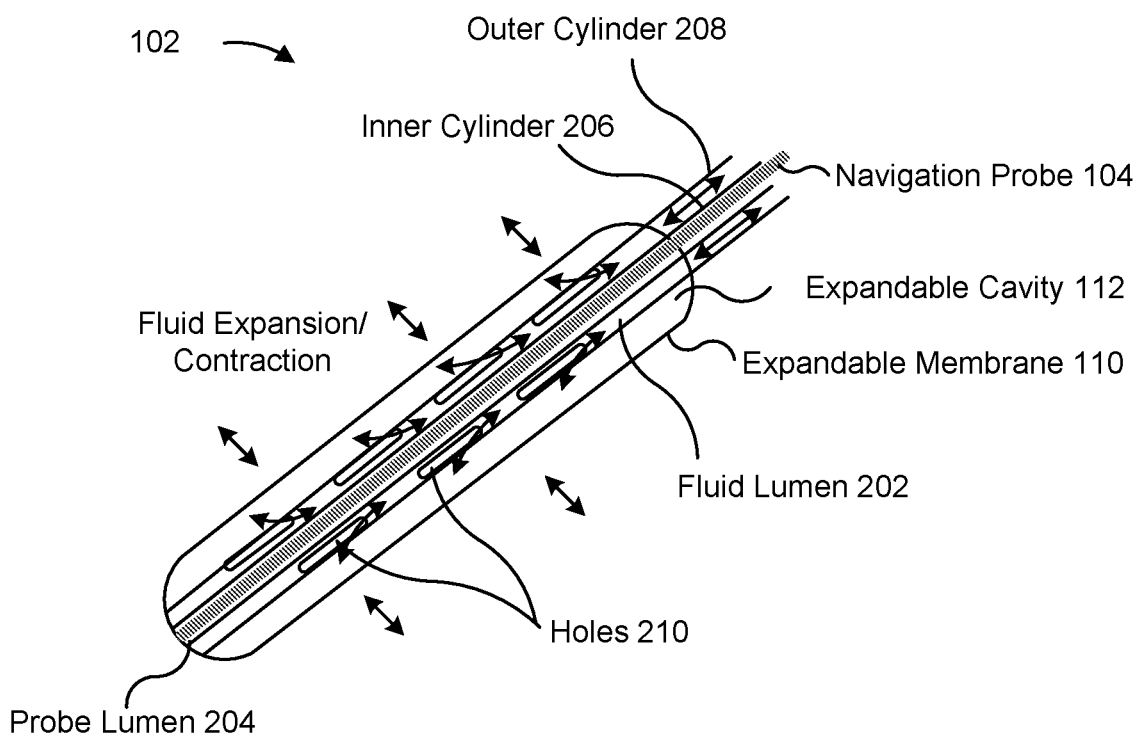
FIGS. 2A and 2B are diagrams of one or more example implementations of a multi-lumen catheter of the surgical instrument system of FIG. 1.
Figure 2B:
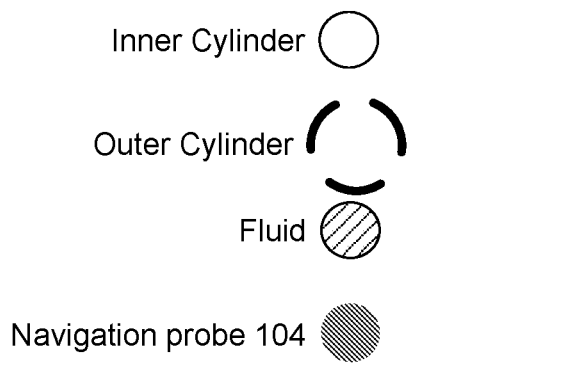
Figure 2B:
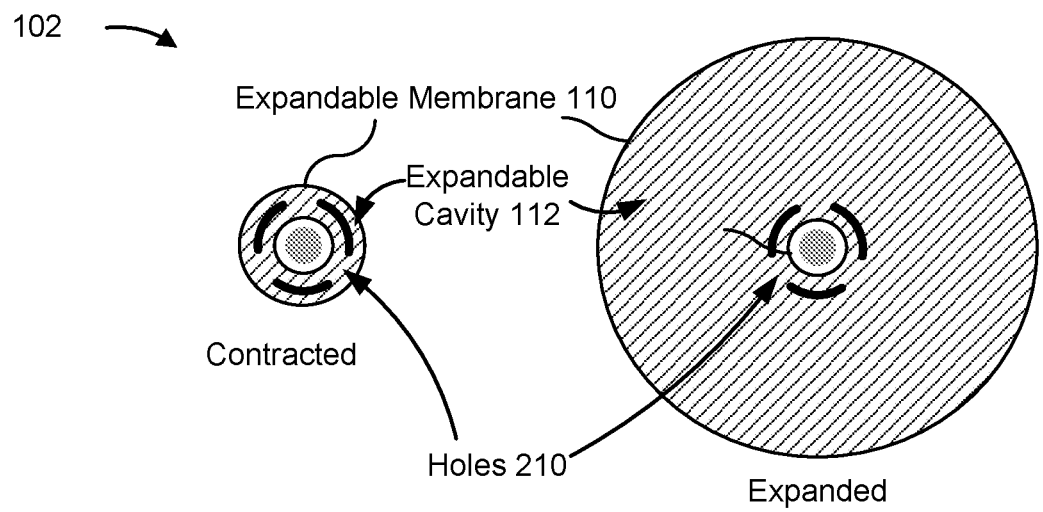

FIGS. 2A and 2B are diagrams of one or more example implementations of a multi-lumen catheter 102 of surgical instrument system 100 of FIG. 1. As shown in FIGS. 2A and 2B, multi-lumen catheter 102 includes a fluid lumen 202 and a probe lumen 204. Probe lumen 204 may be formed by an inner cylinder 206 of multi-lumen catheter 102. Fluid lumen 202 may be formed between inner cylinder 206 and an outer cylinder 208 of multi-lumen catheter 102. Multi-lumen catheter 102 may experience fluid expansion and/or contraction based on the flow of fluid through fluid lumen 202.

As shown in FIG. 2A, probe lumen 204 may receive navigation probe 104. In some implementations, probe lumen 204 be accessible via locking mechanism 124. In such cases, navigation probe 104 may be inserted into probe lumen 204 via locking mechanism 124. One or more dimensions of probe lumen 204 may correspond to one or more dimensions of navigation probe 104. For example, probe lumen 204 may have a diameter that is greater than or equal to a diameter of navigation probe 104 (e.g., to allow space for navigation probe 104 to move within probe lumen 204) and/or a length that is less than or equal to navigation probe 104.

As further shown in FIG. 2A, fluid lumen 202 may be formed between inner cylinder 206 and outer cylinder 208. Outer cylinder 208 may include one or more holes 210 that enable the flow of fluid into expandable cavity 112 during fluid expansion. Holes 210 may be distributed in a particular pattern to control the expansion and/or direction expansion of expandable cavity 112. For example, the plurality of holes may be distributed throughout outer cylinder 208 in a pattern to permit the fluid to relatively uniformly enter expandable cavity 112 and/or cause expandable membrane 110 to apply a relatively uniform force on a tissue that is in contact with expandable membrane 110. In some implementations, fluid lumen 202 may include expandable cavity 112. In other words, expandable cavity 112 and fluid lumen 202 may form a same space that holds the fluid. As described herein, a syringe may be used to control the flow of fluid through fluid lumen 202 and into or from expandable cavity 112.

As shown in FIG. 2B, a cross-sectional view of multi-lumen catheter 102 illustrates that inner cylinder 206 and outer cylinder 208 may be rigid tubal structures. For example, while a diameter of expandable membrane 110 may expand, inner cylinder 206 and outer cylinder 208 of multi-lumen catheter 102 remain at a fixed diameter. Further, as shown by the cross-sectional view, inner cylinder 206 may be solid while outer cylinder 208 includes holes 210 (e.g., may be perforated at the cross-section of the cross-sectional view).

As indicated above, FIGS. 2A and 2B are provided merely as one or more examples. Other examples may differ from what is described with regard to FIGS. 2A and 2B.

Figure 3A:
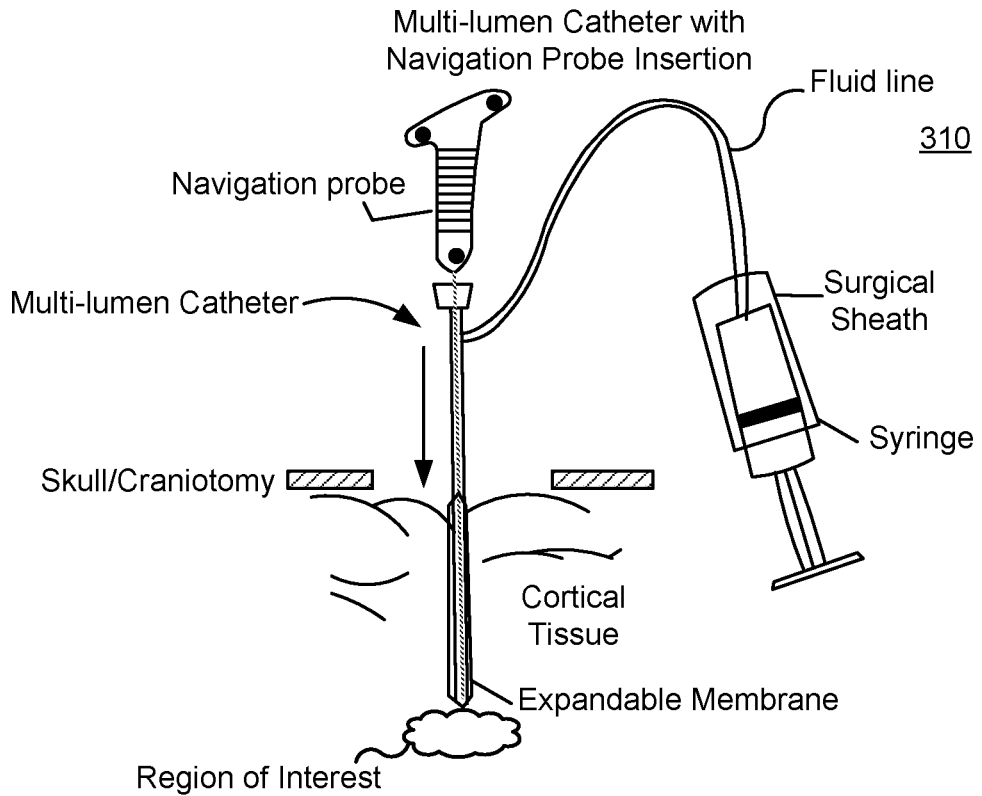
FIGS. 3A-3C are diagrams of one or more example uses of a surgical instrument system described herein.
Figure 3A:
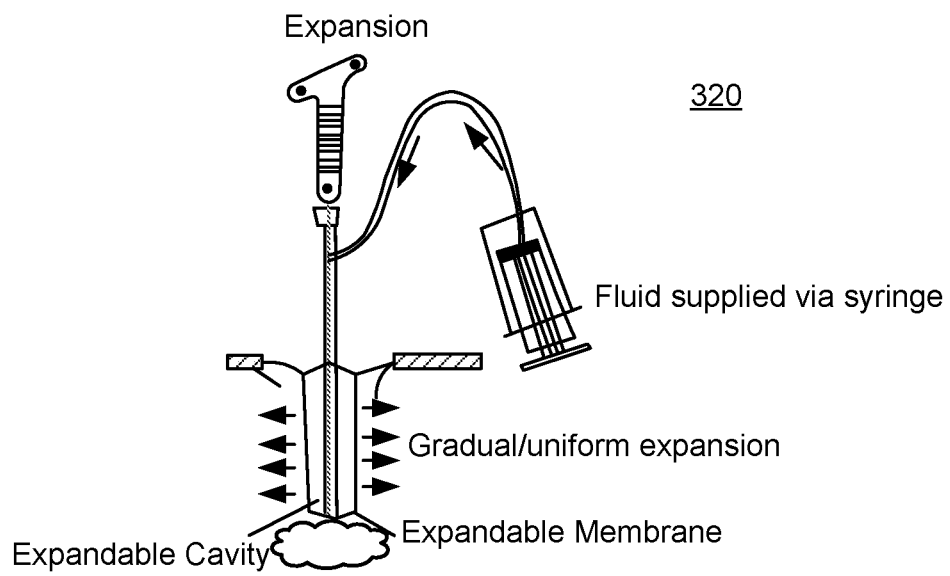
Figure 3B:
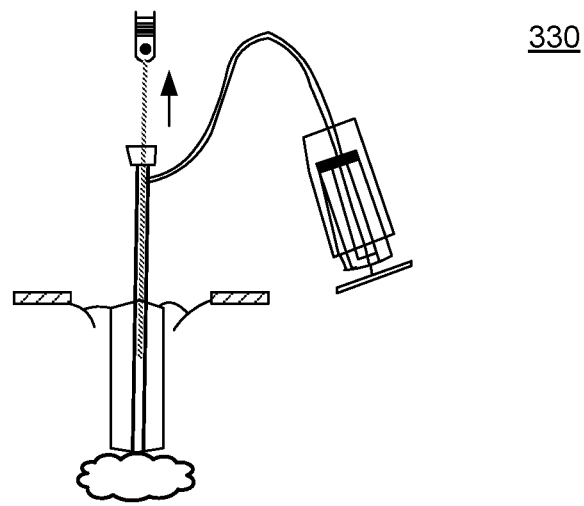
Figure 3B:
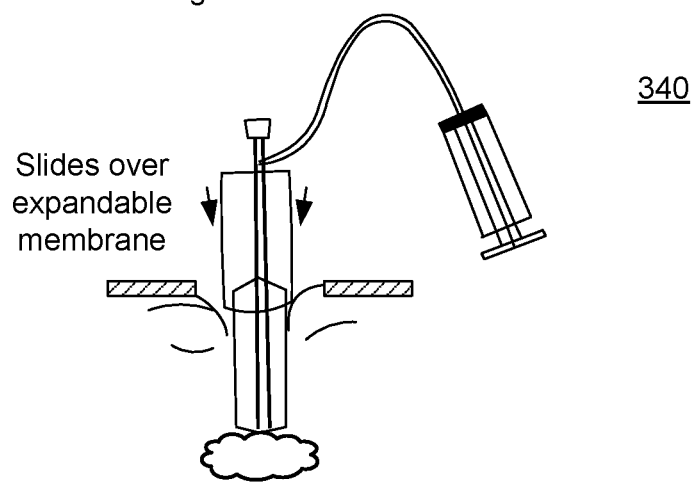
Figure 3C:
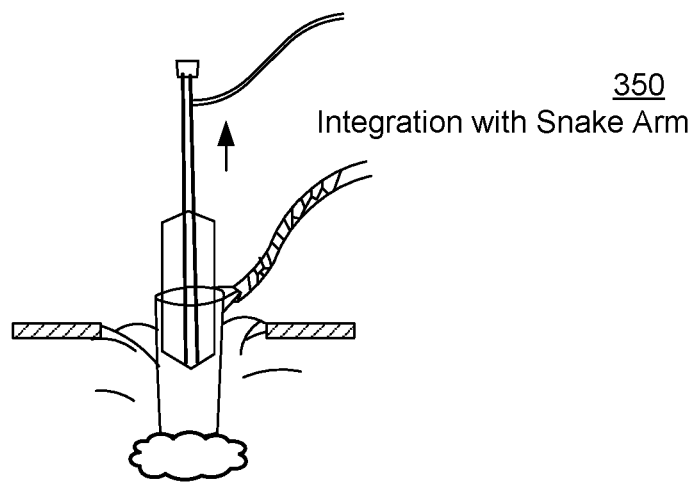
Figure 3C:
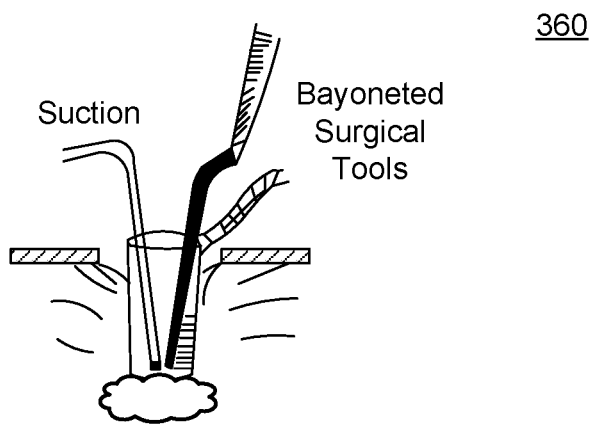

FIGS. 3A-3C are diagrams of one or more example uses of a surgical instrument system (e.g., surgical instrument system 100) described herein. As shown in FIG. 3A, and by reference number 310, a multi-lumen catheter with a navigation probe is inserted into an incision in a cortical tissue. The multi-lumen catheter may be inserted through a craniotomy of a skull and navigated to a region of interest of the cortical tissue. Due to the expandable membrane being contracted, the navigation probe can be navigated through a relatively narrow or minimal incision (or port of entry). Further, this may ease navigation to the region of interest and permit the multi-lumen catheter probe to be removed and/or reinserted multiple times during navigation without increasing risk of injury to the surrounding cortical tissue. As shown, the surgical instrument system includes a fluid line attached to the multi-lumen catheter, a surgical sheath, and a syringe. The multi-lumen catheter includes an expandable membrane that is within the cortical tissue (at least partially) after the multi-lumen catheter is inserted.

As further shown by FIG. 3A, and by reference number 320, fluid is supplied to the multi-lumen catheter via the syringe (e.g., by compressing the syringe). Due to the fluid being supplied to the multi-lumen catheter, the expandable membrane gradually expands (forming an expandable cavity of the multi-lumen catheter), thus applying a relatively uniform force (e.g., a uniform radial force) against the tissue to widen the incision.

As shown by FIG. 3B, and by reference number 330, the navigation probe is removed from the multi-lumen catheter. As further shown by FIG. 3B, and by reference number 340, the surgical sheath is inserted by sliding the surgical sheath over the expandable membrane into the incision. In some implementations, a relatively small portion of the fluid can be removed from the expandable cavity so as to reduce friction when inserting the surgical sheath. In such cases, the removal of the fluid may slightly contract the expandable cavity to permit the surgical sheath to fit between the tissue of the widened incision and the expandable membrane (e.g., before the incision is closed by the tissue naturally closing back together).

As shown by FIG. 3C, and by reference number 350, the multi-lumen catheter is removed from the surgical sheath. In some implementations, prior to removal from the surgical sheath, fluid may be withdrawn from the expandable cavity to reduce friction with the surgical sheath. The surgical sheath may be integrated with a snake arm to permit control of the surgical sheath and/or hold the surgical sheath in place. As further shown by FIG. 3C, and by reference number 360, a corridor of access is created that permits access to the region of interest. For example, additional surgical tools (e.g., a suction tool, one or more bayoneted surgical tools, and/or the like) that can be used, through the surgical sheath, to operate on the region of interest.

As indicated above, FIGS. 3A-3C are provided merely as one or more examples. Other examples may differ from what is described with regard to FIGS. 3A-3C.

Figure 4:
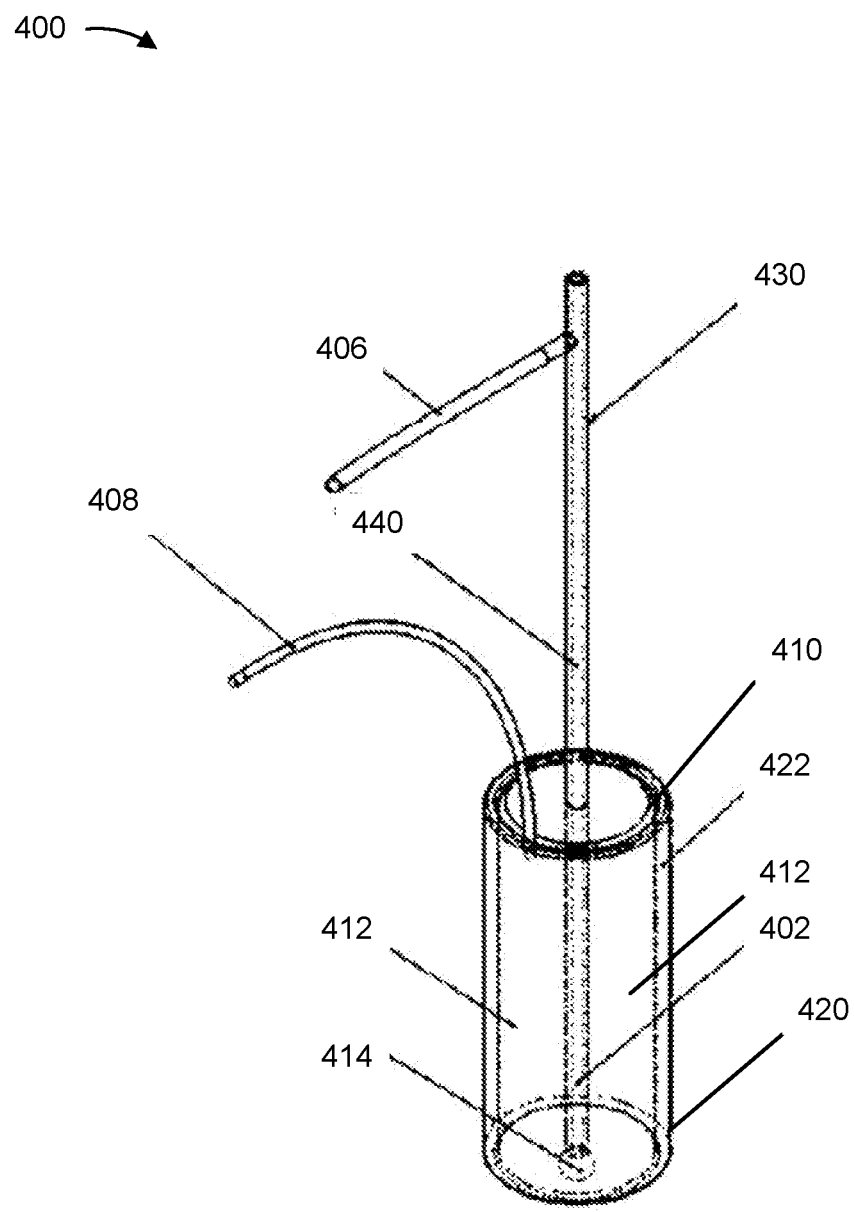
FIG. 4 is a diagram of an example implementation of a surgical instrument system described herein.

FIG. 4 is a diagram of an example implementation of a surgical instrument system 400 described herein. Surgical instrument system 400 includes a multi-lumen catheter 402 (e.g., corresponding to multi-lumen catheter 102 of FIG. 1), a first fluid line 406 (e.g., corresponding to fluid line 106 of FIG. 1), and a second fluid line 408.

Multi-lumen catheter 402 includes an inner expandable membrane 410 that forms an inner expandable cavity 412 and an outer expandable membrane 420 that forms an outer expandable cavity 422. Inner expandable cavity 412 is formed based on a flow of fluid from first fluid line 406 and/or through a fluid lumen 430 of multi-lumen catheter 402. Outer expandable cavity 422 is formed based on a flow of fluid from second fluid line 408. Similar to the surgical instrument system 100 of FIG. 1, a navigation probe (e.g., navigation probe 104) can be received within a probe lumen 440 of multi-lumen catheter 402.

Inner expandable membrane 410 and outer expandable membrane 420 are coaxial and situated at a distal end of multi-lumen catheter 402. For example, inner expandable membrane 410 may be shaped such that inner expandable cavity 412 is cylindrical (e.g., similar to expandable cavity 112), and outer expandable membrane 420 may be shaped such that outer expandable cavity 422 is a tubular shaped membrane that radially surrounds inner expandable cavity 412 to form a flexible tubular structure (e.g., a tubular cushion). Accordingly, there may be a gap between inner expandable cavity 412 and outer expandable cavity 422. As described herein, a surgical sheath (e.g., surgical sheath 108) can be inserted into and/or received within the gap during a surgical procedure associated with tissue, without interfering with or coming into contact with the tissue (e.g., because the outer expandable cavity would be between the tissue and the sheath). In some implementations, inner expandable membrane 410 and outer expandable membrane 420 may have a same length when filled with fluid (e.g., so that a cylindrical structure of first expandable cavity 412 has a same length as a tubular structure of expandable cavity 422). The length may correspond to a length of the surgical sheath.

In some implementations, second fluid line 408 can be detachable from outer expandable membrane 420. For example, second fluid line 408, after being used to fill outer expandable membrane 420 with fluid to form outer expandable cavity 422, can be removed from outer expandable membrane 420 (e.g., an inside of a tubular structure formed by outer expandable cavity 422) to avoid being an obstruction during a surgical procedure (e.g., while outer expandable membrane 420 is to remain in place against tissue associated with the surgical procedure). Second fluid line 408 can be reconnected following a portion of the surgical procedure to relatively slowly withdraw fluid from outer expandable membrane 420 to correspondingly decrease a diameter of outer expandable cavity 422, thereby reducing pressure against the tissue.

As indicated above, FIG. 4 is provided merely as one or more examples. Other examples may differ from what is described with regard to FIG. 4.

Figure 5A:
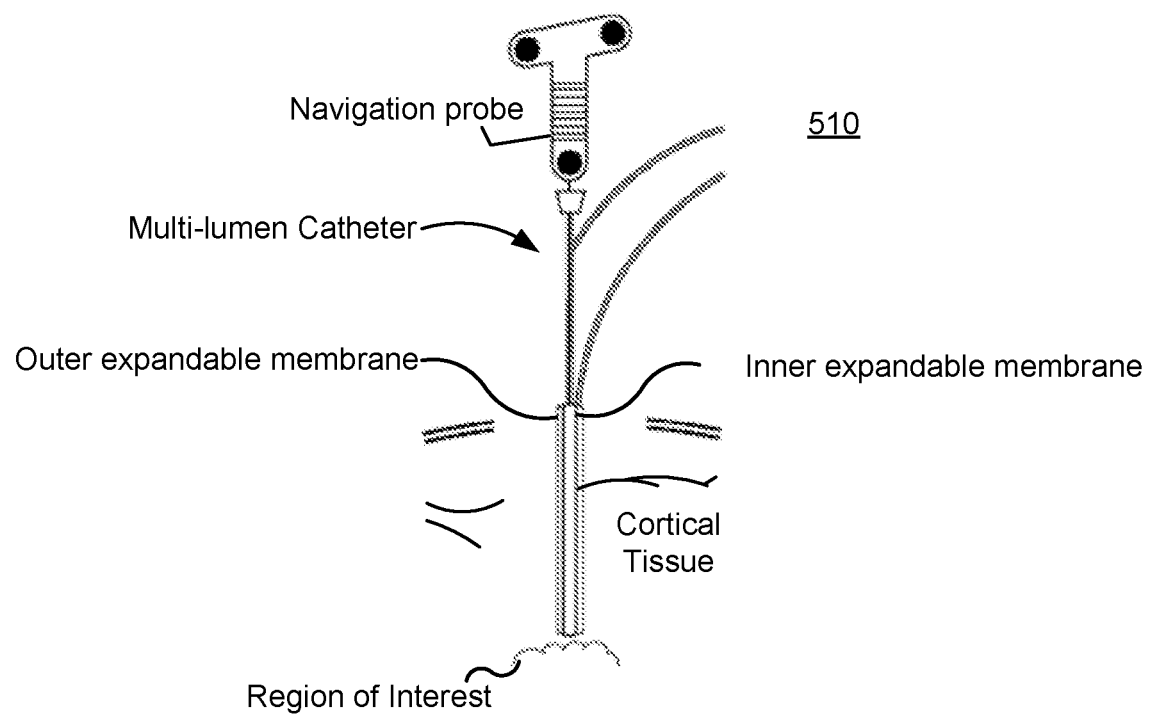
FIGS. 5A-5C are diagrams of one or more example uses of a surgical instrument system described herein.
Figure 5A:
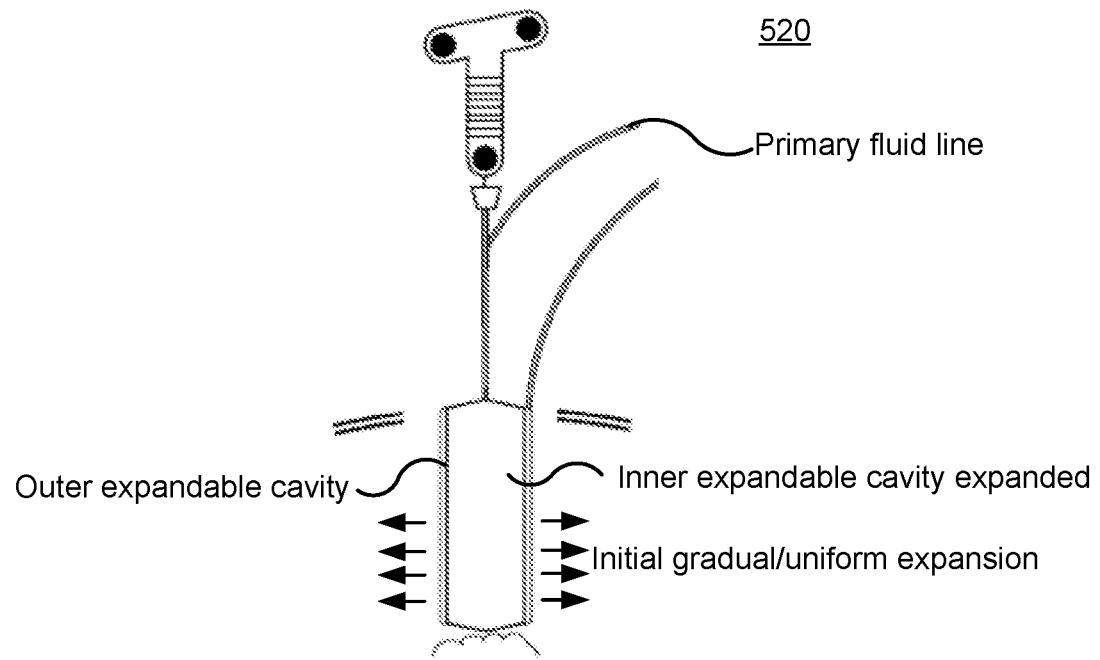
Figure 5B:
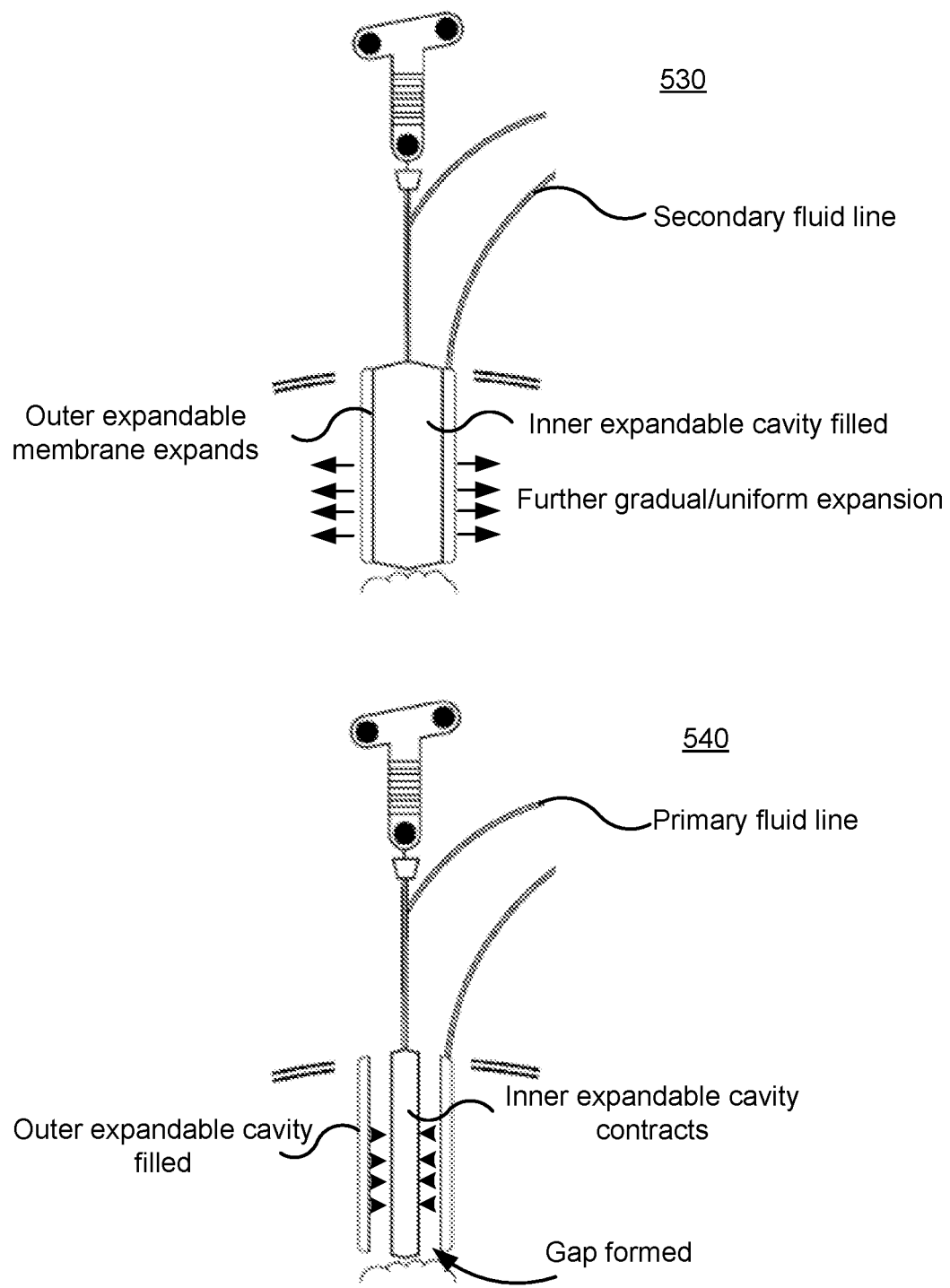
Figure 5C:
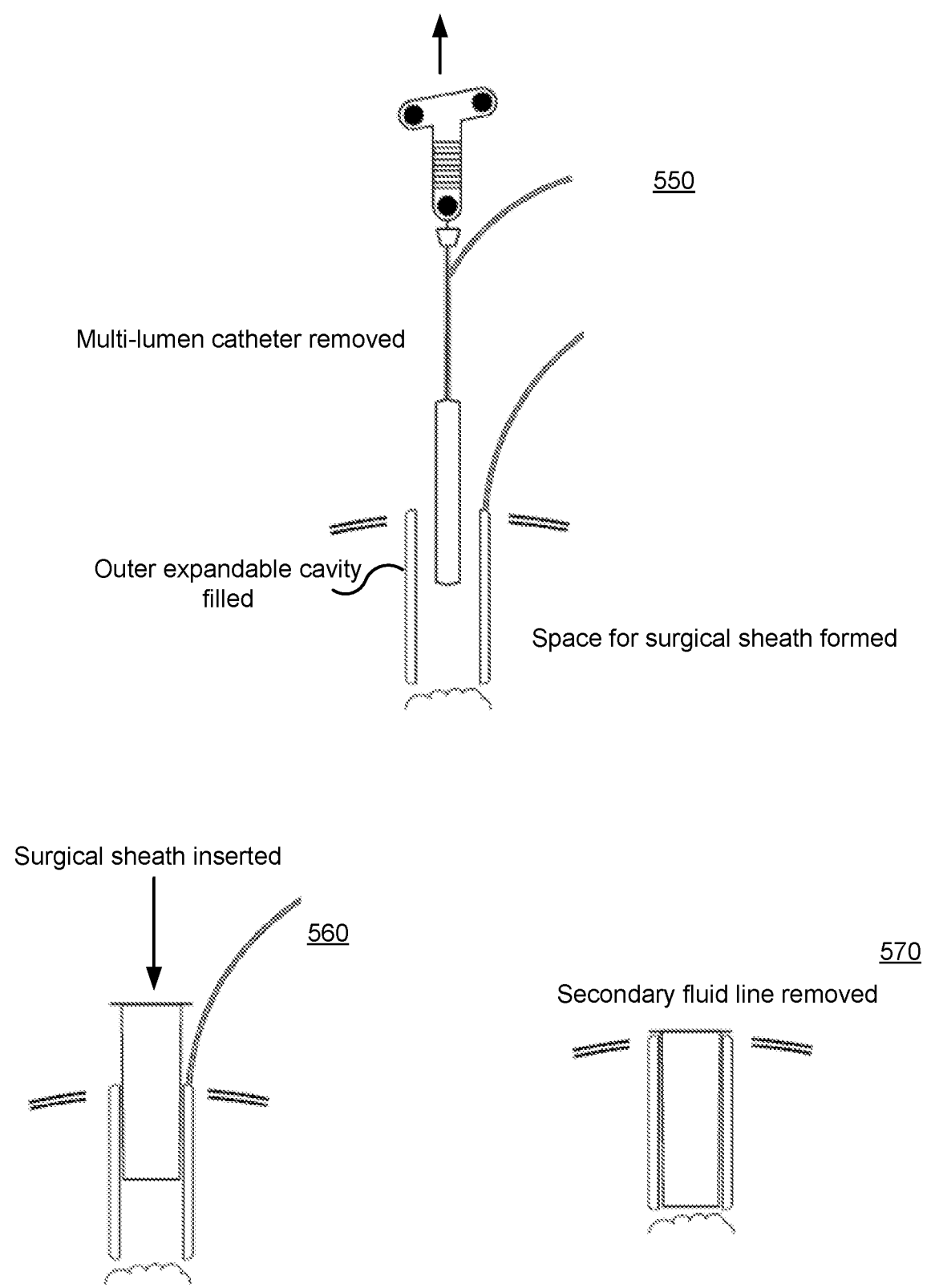

FIGS. 5A-5C are diagrams of one or more example uses of a surgical instrument system (e.g., surgical instrument system 400) described herein. Certain examples described in connection with FIGS. 5A-5C may be similarly performed during corresponding operations described in connection with FIGS. 3A-3C. As shown in FIG. 5A, and by reference number 510, a surgical instrument that includes a multi-lumen catheter (e.g., multi-lumen catheter 402) (e.g., with a navigation probe and an inner expandable membrane) and an outer expandable membrane is inserted into an incision in a cortical tissue (e.g., similar to operations described in connection with reference number 310). The multi-lumen catheter can be used to position the outer expandable membrane in place (which is fit around the inner expandable membrane prior to and/or during insertion), within the incision to ultimately permit access to the region of interest, as described herein.

As further shown by FIG. 5A, and by reference number 520, fluid is supplied, from the primary fluid line to the multi-lumen catheter. Accordingly, the inner expandable membrane gradually expands (increasing a volume of an inner expandable cavity of the multi-lumen catheter and/or a diameter of an outer expandable cavity), thus causing the outer expandable membrane to apply a relatively uniform force (e.g., a uniform radial force) against the tissue to widen the incision.

As shown in FIG. 5B, and by reference number 530, with the inner expandable cavity filled with fluid, fluid is supplied from the secondary fluid line to the outer expandable cavity. Accordingly, the outer expandable membrane further expands (e.g., increasing a volume of the outer expandable cavity) to form a flexible tubular structure (e.g., a tubular cushion) that applies relatively uniform force against the tissue. In this way, the outer expandable membrane may further widen the incision, provide a flexible barrier between the tissue and the inner expandable cavity, and/or reduce pressure on the inner expandable cavity (e.g., by withstanding responsive forces from any contraction of the tissue).

As further shown in FIG. 5B, and by reference number 540, with the outer expandable membrane is filled with fluid, the fluid in the inner expandable cavity is withdrawn, via the primary fluid line (e.g., using the syringe) and/or through the multi-lumen catheter. Accordingly, the inner expandable cavity contracts, reducing friction between the inner expandable membrane and the outer expandable membrane and allowing for movement of the inner expandable membrane relative to the outer expandable membrane. If a sufficient amount of fluid in the inner expandable cavity is withdrawn, a gap may be formed between the inner expandable membrane and the outer expandable membrane. The presence of the fluid within the outer expandable cavity forms a tubular structure that has a degree of strength or rigidity to form a flexible barrier between the tissue and the inner expandable cavity and/or that would prevent pressure from the tissue from enclosing the tubular structure of the outer expandable cavity.

As shown by FIG. 5C, and by reference number 550, the multi-lumen catheter is removed from the tubular structure formed by the outer expandable cavity, with the outer expandable cavity being retained within the incision (e.g., to withstand pressure from the tissue). Accordingly, a space is created for the surgical sheath. As shown by reference number 560, the surgical sheath is inserted by sliding the surgical sheath into the tubular structure formed by the outer expandable cavity, which serves as a flexible barrier (e.g., cushion or buffer) between the rigid surgical sheath and the tissue. Accordingly, the outer expandable membrane and/or outer expandable cavity may cushion any movement of the surgical sheath during a surgical procedure, while the surgical sheath provides a rigid corridor of access to the region of interest and serves as a protective barrier to prevent any other surgical instruments from damaging (e.g., puncturing) the outer expandable membrane. As shown by reference number 570, the secondary fluid line is removed from the outer expandable cavity to avoid being an obstruction during the surgical procedure (e.g., to avoid being in the way of additional surgical tools). In this way, a corridor of access is created by the surgical instrument system that permits access, via the surgical sheath and/or the outer expandable cavity, to the region of interest.

Accordingly, as described herein, a surgical instrument system is provided that enables access to a region of interest within tissue. The surgical instrument system can create an opening in the tissue by applying a relatively uniform force to the tissue of an incision, thus preventing any excessive and/or focused forces on one or more areas of the tissue, leading to further injury to the tissue and/or the patient.

Figure 6:
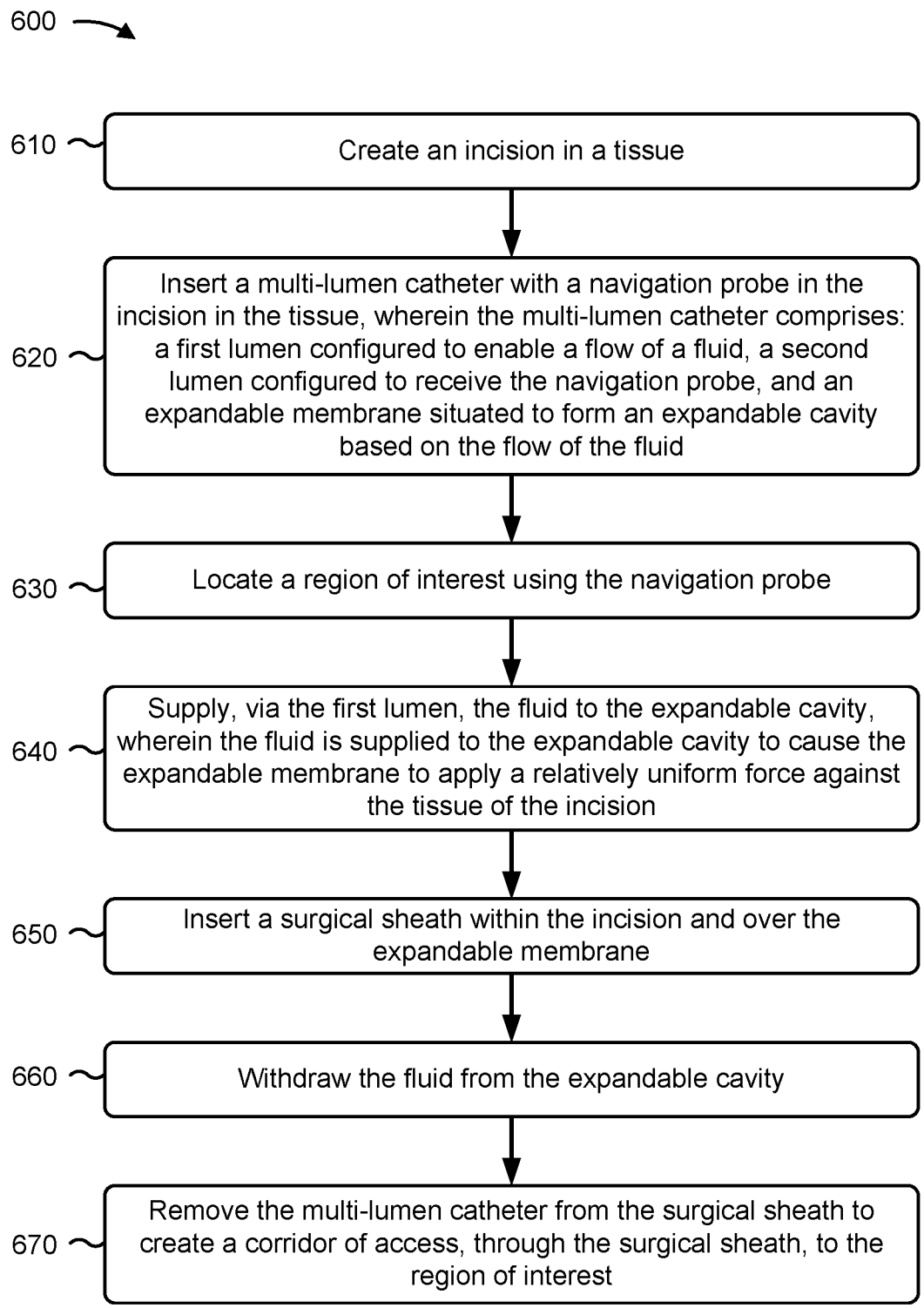
FIGS. 6 and 7 are flowcharts of one or more example processes associated with accessing a region of interest using a surgical instrument system described herein.

FIG. 6 is a flowchart of an example surgical procedure 600 associated with accessing a region of interest, as described herein. In some implementations, one or more process blocks of FIG. 6 may be performed using a surgical instrument system (e.g., surgical instrument system 100, surgical instrument system 400, and/or the like). In some implementations, one or more process blocks of FIG. 6 may be performed in association with one or more other surgical procedures (e.g., a craniotomy, a lesion extraction procedure, and/or the like), using one or more other surgical instruments and/or surgical tools other than the surgical instrument system, and/or the like.

As shown in FIG. 6, process 600 may include creating an incision in a tissue (block 610). For example, an incision may be created in a tissue to receive one or more components of the surgical instrument system, as described above.

As further shown in FIG. 6, process 600 may include inserting a multi-lumen catheter with a navigation probe in the incision in the tissue, wherein the multi-lumen catheter comprises a first lumen configured to enable a flow of a fluid, a second lumen configured to receive the navigation probe and an expandable membrane situated to form an expandable cavity based on the flow of the fluid (block 620). For example, a multi-lumen catheter and/or a navigation probe of the surgical instrument system may be inserted in the incision in the tissue, as described above. The multi-lumen catheter of the surgical instrument system may include a first lumen configured to enable a flow of a fluid, a second lumen configured to receive the navigation probe, and an expandable membrane situated to form an expandable cavity based on the flow of the fluid, as described above.

As further shown in FIG. 6, process 600 may include locating a region of interest using the navigation probe (block 630). For example, one or more components of the surgical instrument system may be used to locate a region of interest using the navigation probe of the surgical instrument system, as described above.

As further shown in FIG. 6, process 600 may include supplying, via the first lumen, the fluid to the expandable cavity wherein the fluid is supplied to the expandable cavity to cause the expandable membrane to apply a relatively uniform force against the tissue of the incision (block 640). For example, one or more components of the surgical instrument system may be used to supply, via the first lumen, the fluid to the expandable cavity, as described above. The fluid may be supplied to the expandable cavity to cause the expandable membrane to apply a relatively uniform force against the tissue of the incision.

As further shown in FIG. 6, process 600 may include inserting a surgical sheath within the incision and over the expandable membrane (block 650). For example, a surgical sheath of the surgical instrument system may be inserted within the incision and over the expandable membrane, as described above.

As further shown in FIG. 6, process 600 may include withdrawing the fluid from the expandable cavity (block 660). For example, one or more components of the surgical instrument system may be used to withdraw the fluid from the expandable cavity, as described above.

As further shown in FIG. 6, process 600 may include removing the multi-lumen catheter from the surgical sheath to create a corridor of access, through the surgical sheath, to the region of interest (block 670). For example, the multi-lumen catheter, of the surgical instrument system, may be removed from the surgical sheath to create a corridor of access, through the surgical sheath, to the region of interest, as described above.

Process 600 may include additional implementations, such as any single implementation or any combination of implementations described below and/or in connection with one or more other processes described elsewhere herein.

In some implementations, the first lumen is formed from a rigid tubular structure of the multi-lumen catheter. In some implementations, the rigid tubular structure of the multi-lumen catheter comprises an outer cylinder that includes a plurality of holes to permit the flow of the fluid and an inner cylinder. In some implementations, the second lumen is formed by the inner cylinder of the rigid tubular structure. In some implementations, the plurality of holes are distributed in a pattern to permit the fluid to uniformly enter the expandable cavity.

In some implementations, the second lumen is coaxially within the first lumen. In some implementations, the expandable membrane has a length that is greater than or equal to a depth of the region of interest relative to a surface of the tissue. In some implementations, the expandable membrane is circumferentially attached to the first lumen at a distal end of the first lumen. In some implementations, the expandable membrane is circumferentially attached to the first lumen between the distal end of the first lumen and a locking mechanism that attaches the navigation probe to the multi-lumen catheter when the navigation probe is received within the second lumen.

In some implementations, a fluid line is coupled to the first lumen at a first end of the fluid line. In some implementations, a syringe is coupled to the fluid line at a second end of the fluid line that is opposite the first end of the fluid line, and the syringe is used to at least one of: supply the fluid to the expandable cavity or withdraw the fluid from the expandable cavity. In some implementations, when the expandable cavity is supplied with the fluid, the expandable membrane is configured to apply the relatively uniform force to any part of the tissue of the incision that is in contact with the expandable membrane.

In some implementations, when the expandable cavity is supplied with the fluid, the expandable cavity creates an opening in the tissue via the relatively uniform force. In some implementations, the opening comprises a widening of the incision, and the expandable cavity is configured to enable the surgical sheath to be inserted into the opening to create the corridor of access through the surgical sheath to enable an individual to access the region of interest through the surgical sheath.

In some implementations, the navigation probe facilitates an ability to locate the region of interest via digital image processing. In some implementations, the multi-lumen catheter comprises a locking mechanism that permits the navigation probe to be attached to the multi-lumen catheter to cause movement of the navigation probe and to cause corresponding movement of the multi-lumen catheter. In some implementations, the locking mechanism permits the navigation probe to be detached from the multi-lumen catheter.

Although FIG. 6 shows example blocks of process 600, in some implementations, process 600 may include additional blocks, fewer blocks, different blocks, or differently arranged blocks than those depicted in FIG. 6. Additionally, or alternatively, two or more of the blocks of process 600 may be performed in parallel.

Figure 7:
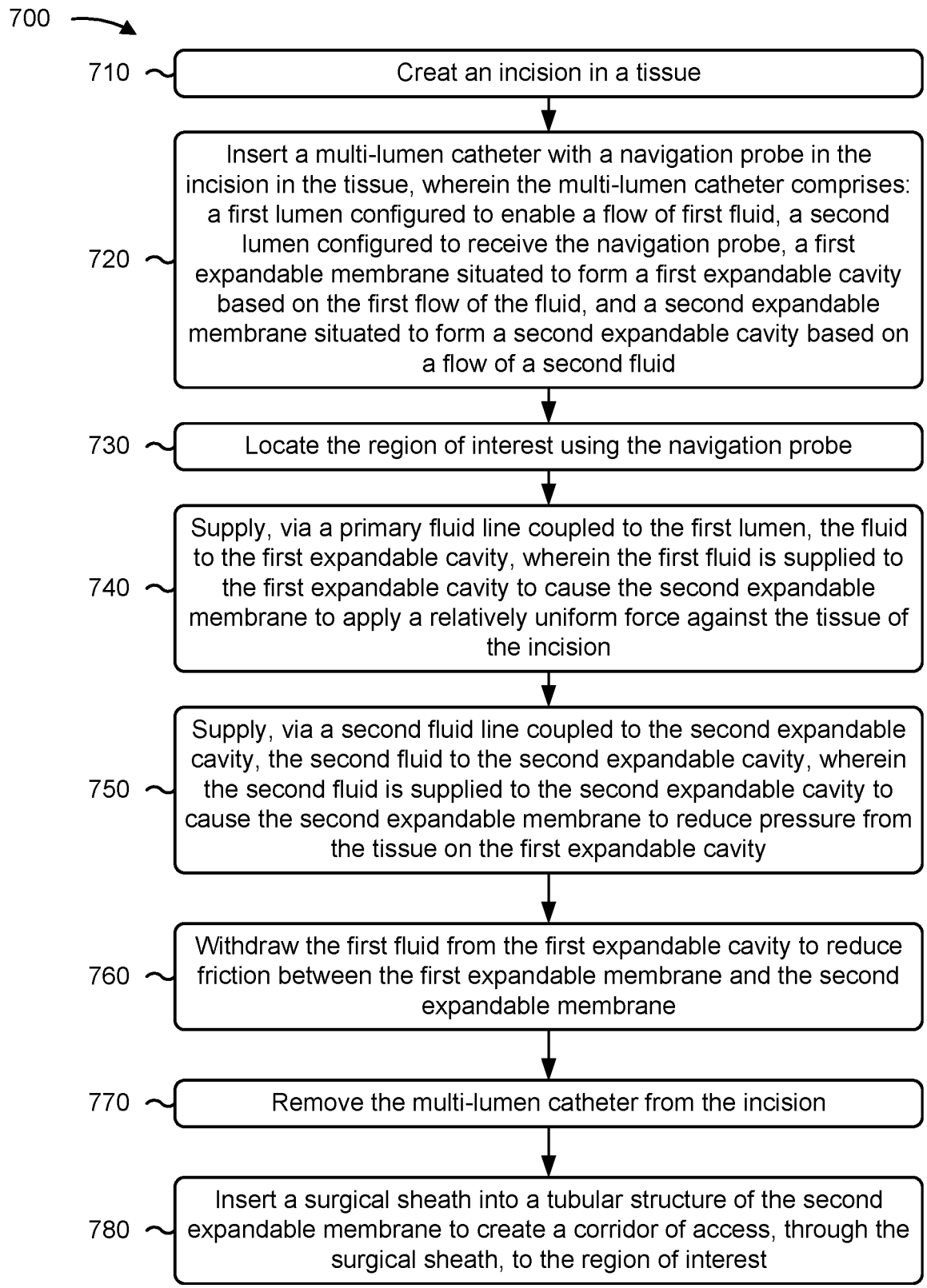

FIG. 7 is a flowchart of an example surgical procedure 700 associated with accessing a region of interest, as described herein. In some implementations, one or more process blocks of FIG. 7 may be performed using a surgical instrument system (e.g., surgical instrument system 100, surgical instrument system 400, and/or the like). In some implementations, one or more process blocks of FIG. 7 may be performed in association with one or more other surgical procedures (e.g., a craniotomy, a lesion extraction procedure, and/or the like), using one or more other surgical instruments and/or surgical tools other than the surgical instrument system, and/or the like.

As shown in FIG. 7, process 700 may include creating an incision in a tissue (block 710). For example, an incision may be created in a tissue to receive one or more components of the surgical instrument system, as described above. As further shown in FIG. 7, process 700 may include inserting a surgical instrument with a navigation probe in the incision in the tissue, wherein the surgical instrument comprises: a multi-lumen catheter that includes: a first lumen configured to enable a flow of first fluid, a second lumen configured to receive the navigation probe, a first expandable membrane situated to form a first expandable cavity based on the first flow of the fluid, and a second expandable membrane situated to form a second expandable cavity based on a flow of a second fluid (block 720). As further shown in FIG. 7, process 700 may include locating the region of interest using the navigation probe (block 730).

As further shown in FIG. 7, process 700 may include supplying, via a primary fluid line coupled to the first lumen, the fluid to the first expandable cavity, wherein the first fluid is supplied to the first expandable cavity to cause the second expandable membrane to apply a relatively uniform force against the tissue of the incision (block 740). As further shown in FIG. 7, process 700 may include supplying, via a second fluid line coupled to the second expandable cavity, the second fluid to the second expandable cavity, wherein the second fluid is supplied to the second expandable cavity to cause the second expandable membrane to form a tubular structure that provides a flexible barrier between the tissue and the first expandable cavity (block 750).

As further shown in FIG. 7, process 700 may include withdrawing the first fluid from the first expandable cavity to reduce friction between the first expandable membrane and the tubular structure formed by the second expandable membrane (block 760). As further shown in FIG. 7, process 700 may include removing the multi-lumen catheter from the tubular structure without removing the second expandable membrane from the incision (block 770). As further shown in FIG. 7, process 700 may include inserting a surgical sheath into the tubular structure to create a corridor of access, through the surgical sheath, to the region of interest (block 780).

Although FIG. 7 shows example blocks of process 700, in some implementations, process 700 may include additional blocks, fewer blocks, different blocks, or differently arranged blocks than those depicted in FIG. 7. Additionally, or alternatively, two or more of the blocks of process 700 may be performed in parallel.

The foregoing disclosure provides illustration and description but is not intended to be exhaustive or to limit the implementations to the precise forms disclosed. Modifications and variations may be made in light of the above disclosure or may be acquired from practice of the implementations.

As used herein, the term "component" is intended to be broadly construed as hardware, firmware, and/or a combination of hardware and software.

Even though particular combinations of features are recited in the claims and/or disclosed in the specification, these combinations are not intended to limit the disclosure of various implementations. In fact, many of these features may be combined in ways not specifically recited in the claims and/or disclosed in the specification. Although each dependent claim listed below may directly depend on only one claim, the disclosure of various implementations includes each dependent claim in combination with every other claim in the claim set.

No element, act, or instruction used herein should be construed as critical or essential unless explicitly described as such. Also, as used herein, the articles "a" and "an" are intended to include one or more items and may be used interchangeably with "one or more." Furthermore, as used herein, the term "set" is intended to include one or more items (e.g., related items, unrelated items, a combination of related and unrelated items, etc.), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise.

What is claimed is:

1. A surgical instrument to enable access to a region of interest within a tissue, the surgical instrument comprising:
    a multi-lumen catheter configured to be inserted within the tissue, the multi-lumen catheter comprising:
        a first lumen configured to enable a flow of a fluid,
        a second lumen configured to receive a navigation probe that facilitates location of the region of interest within the tissue, and
        an expandable membrane situated toward a distal end of the first lumen to form an expandable cavity,
            wherein the expandable cavity is configured to expand or contract based on the flow of the fluid through the first lumen; and
    a fluid line, coupled to the first lumen, that is configured to:
        supply the fluid to the first lumen to enable the expandable cavity to expand, and
        withdraw the fluid from the first lumen to enable the expandable cavity to contract,
            wherein the fluid line is configured to withdraw the fluid from the expandable cavity, into the first lumen, and via the fluid line.

2. The surgical instrument of claim 1, wherein the first lumen is formed from a rigid tubular structure of the multi-lumen catheter,
    wherein the rigid tubular structure of the multi-lumen catheter comprises:
        an outer cylinder that includes a plurality of holes to permit the flow of the fluid, and
        an inner cylinder,
            wherein the first lumen is situated between the outer cylinder and the inner cylinder of the rigid tubular structure.

3. The surgical instrument of claim 2, wherein the second lumen is formed by the inner cylinder of the rigid tubular structure.

4. The surgical instrument of claim 2, wherein the plurality of holes are distributed in a pattern to permit the fluid to uniformly enter the expandable cavity.

5. The surgical instrument of claim 1, wherein the second lumen is coaxially within the first lumen.

6. The surgical instrument of claim 1, wherein the expandable membrane has a length that is greater than a depth of the region of interest relative to a surface of the tissue.

7. The surgical instrument of claim 1, wherein the expandable membrane is circumferentially attached to the first lumen at the distal end of the first lumen, and
    circumferentially attached to the first lumen between the distal end of the first lumen and a locking mechanism that attaches the navigation probe to the multi-lumen catheter when the navigation probe is received within the second lumen.

8. The surgical instrument of claim 1, wherein the fluid line is coupled to the first lumen at a first end, and
    wherein the surgical instrument further includes:
        a syringe coupled to the fluid line at a second end of the fluid line that is opposite the first end of the fluid line,
            wherein the syringe is configured to control the flow of the fluid.

9. The surgical instrument of claim 1, wherein the distal end is configured to be inserted within the tissue and the expandable cavity, when expanded within the tissue, is configured to create a corridor of access in the tissue.

10. The surgical instrument of claim 1, wherein, when the expandable cavity is supplied with the fluid, the expandable membrane is configured to apply a relatively uniform force to any part of the tissue in contact with the expandable membrane.

11. The surgical instrument of claim 1, wherein, when the expandable cavity is supplied with the fluid, the expandable cavity creates an opening in the tissue, and
    wherein the expandable cavity is configured to enable a surgical sheath to be inserted into the opening to create a corridor of access through the surgical sheath and enable an individual to access the region of interest via the corridor of access.

12. The surgical instrument of claim 1, wherein the navigation probe facilitates an ability to locate the region of interest via digital image processing.

13. The surgical instrument of claim 1, wherein the multi-lumen catheter comprises a locking mechanism that permits the navigation probe to be attached to the multi-lumen catheter to cause movement of the navigation probe to cause corresponding movement of the multi-lumen catheter, and
    wherein the locking mechanism permits the navigation probe to be detached from the multi-lumen catheter.

14. A surgical instrument system comprising:
    a navigation probe that enables a region of interest to be located within a tissue;
    a multi-lumen catheter configured to receive the navigation probe,
        wherein the multi-lumen catheter comprises:
            a first lumen configured to enable a flow of a fluid,
            a second lumen configured to receive the navigation probe, and an expandable membrane situated toward a distal end of the first lumen to form an expandable cavity,
wherein the expandable cavity is configured to expand or contract based on the flow of the fluid through the first lumen;
a fluid line, coupled to the first lumen, that is configured to:
supply the fluid to the first lumen to enable the expandable cavity to expand, and
withdraw the fluid from the first lumen to enable the expandable cavity to contract,
wherein the fluid line is configured to withdraw the fluid from the expandable cavity, into the first lumen, and via the fluid line; and
a surgical sheath configured to be received within the tissue when the expandable cavity is expanded,
wherein the expandable membrane, when the expandable cavity is expanded and the surgical sheath is received within the tissue, is received within the surgical sheath.

15. The surgical instrument system of claim 14, wherein, when the expandable cavity is contracted or the multi-lumen catheter is removed from the tissue, the surgical sheath forms a corridor of access, in the tissue, to the region of interest.

16. The surgical instrument system of claim 14, wherein the first lumen is formed from a rigid tubular structure of the multi-lumen catheter,
wherein the rigid tubular structure of the multi-lumen catheter comprises:
an outer cylinder that includes a plurality of holes to permit the flow of the fluid, and
an inner cylinder,
wherein the first lumen is situated between the outer cylinder and the inner cylinder of the rigid tubular structure.

17. The surgical instrument system of claim 16, wherein the second lumen is formed by the inner cylinder of the rigid tubular structure.

18. The surgical instrument system of claim 16, wherein the plurality of holes are distributed in a pattern to permit the fluid to uniformly enter the expandable cavity.

19. The surgical instrument system of claim 14, wherein the second lumen is coaxially within the first lumen.

20. The surgical instrument system of claim 14, wherein the expandable membrane has a length that is greater than a depth of the region of interest relative to a surface of the tissue.

21. The surgical instrument system of claim 14, wherein the expandable membrane is circumferentially attached to the first lumen at the distal end of the first lumen, and
and circumferentially attached to the first lumen between the distal end of the first lumen and a locking mechanism that attaches the navigation probe to the multi-lumen catheter when the navigation probe is received within the second lumen.

22. The surgical instrument system of claim 14, wherein the fluid line is coupled to the first lumen at a first end of the fluid line, and
wherein the surgical instrument further includes:
a syringe coupled to the fluid line at a second end of the fluid line that is opposite the first end of the fluid line, wherein the syringe is configured to control the flow of the fluid.

23. The surgical instrument system of claim 14, wherein the distal end is configured to be inserted within the tissue and the expandable cavity, when expanded within the tissue, is configured to create a corridor of access in the tissue.

24. The surgical instrument system of claim 14, wherein, when the expandable cavity is supplied with the fluid, the expandable membrane is configured to apply a relatively uniform force to any part of the tissue in contact with the expandable membrane.

25. The surgical instrument system of claim 14, wherein, when the expandable cavity is supplied with the fluid, the expandable cavity creates an opening in the tissue, and
wherein the expandable cavity is configured to enable the surgical sheath to be inserted into the opening to create a corridor of access through the surgical sheath and to enable an individual to access the region of interest via the corridor of access.

26. The surgical instrument system of claim 14, wherein the navigation probe facilitates an ability to locate the region of interest via digital image processing.

27. The surgical instrument system of claim 14, wherein the multi-lumen catheter comprises a locking mechanism that permits the navigation probe to be attached to the multi-lumen catheter to cause movement of the navigation probe to cause corresponding movement of the multi-lumen catheter, and
wherein the locking mechanism permits the navigation probe to be detached from the multi-lumen catheter.

28. A surgical procedure associated with accessing a region of interest comprising:
creating an incision in a tissue;
inserting a multi-lumen catheter with a navigation probe in the incision in the tissue,
wherein the multi-lumen catheter comprises:
a first lumen configured to enable a flow of a fluid,
a second lumen configured to receive the navigation probe, and
an expandable membrane situated to form an expandable cavity based on the flow of the fluid;
locating the region of interest using the navigation probe;
supplying, via the first lumen, the fluid to the expandable cavity,
wherein the fluid is supplied to the expandable cavity to cause the expandable membrane to apply a relatively uniform force against the tissue of the incision;
inserting a surgical sheath within the incision and over the expandable membrane;
withdrawing the fluid from the expandable cavity,
wherein the fluid is withdrawn from the expandable cavity, into the first lumen, and into a fluid line coupled to the first lumen; and
removing the multi-lumen catheter from the surgical sheath to create a corridor of access, through the surgical sheath, to the region of interest.

29. The surgical procedure of claim 28, wherein the first lumen is formed from a rigid tubular structure of the multi-lumen catheter,
wherein the rigid tubular structure of the multi-lumen catheter comprises:
an outer cylinder that includes a plurality of holes to permit the flow of the fluid, and
an inner cylinder,
wherein the first lumen is situated between the outer cylinder and the inner cylinder of the rigid tubular structure.

30. The surgical procedure of claim 29, wherein the second lumen is formed by the inner cylinder of the rigid tubular structure.

31. The surgical procedure of claim 29, wherein the plurality of holes are distributed in a pattern to permit the fluid to uniformly enter the expandable cavity.

32. The surgical procedure of claim 28, wherein the second lumen is coaxially within the first lumen.

33. The surgical procedure of claim 28, wherein the expandable membrane has a length that is greater than or equal to a depth of the region of interest relative to a surface of the tissue.

34. The surgical procedure of claim 28, wherein the expandable membrane is circumferentially attached to the first lumen at a distal end of the first lumen, and
wherein the expandable membrane is circumferentially attached to the first lumen between the distal end of the first lumen and a locking mechanism that attaches the navigation probe to the multi-lumen catheter when the navigation probe is received within the second lumen.

35. The surgical procedure of claim 28, wherein the fluid line is coupled to the first lumen at a first end of the fluid line, and
wherein a syringe is coupled to the fluid line at a second end of the fluid line that is opposite the first end of the fluid line,
wherein the syringe is used to at least one of:
supply the fluid to the expandable cavity, or
withdraw the fluid from the expandable cavity.

36. The surgical procedure of claim 28, wherein, when the expandable cavity is supplied with the fluid, the expandable membrane is configured to apply the relatively uniform force to any part of the tissue of the incision that is in contact with the expandable membrane.

37. The surgical procedure of claim 28, wherein, when the expandable cavity is supplied with the fluid, the expandable cavity creates an opening in the tissue via the relatively uniform force,
wherein the opening comprises a widening of the incision, and
wherein the expandable cavity is configured to enable the surgical sheath to be inserted into the opening to create the corridor of access through the surgical sheath to enable an individual to access the region of interest through the surgical sheath.

38. The surgical procedure of claim 28, wherein the navigation probe facilitates an ability to locate the region of interest via digital image processing.

39. The surgical procedure of claim 28, wherein the multi-lumen catheter comprises a locking mechanism that permits the navigation probe to be attached to the multi-lumen catheter to cause movement of the navigation probe and to cause corresponding movement of the multi-lumen catheter, and
wherein the locking mechanism permits the navigation probe to be detached from the multi-lumen catheter.

40. A surgical instrument system comprising:
a navigation probe that enables a region of interest to be located within a tissue;
a multi-lumen catheter configured to receive the navigation probe,
wherein the multi-lumen catheter comprises:
a first lumen configured to enable a flow of a first fluid,
a second lumen configured to receive the navigation probe, and
a first expandable membrane situated toward a distal end of the first lumen to form a first expandable cavity,
wherein the first expandable cavity is configured to expand or contract based on the flow of the first fluid through the first lumen;
a primary fluid line, coupled to the first lumen, that is configured to:
supply the first fluid to the first lumen to enable the first expandable cavity to expand, or
withdraw the first fluid from the first lumen to enable the first expandable cavity to contract;
a second expandable membrane to form a second expandable cavity,
wherein the second expandable membrane is coaxial to the first expandable membrane at the distal end of the first lumen, and
wherein the second expandable cavity is configured to expand or contract based on a flow of second fluid to or from the second expandable cavity;
a secondary fluid line, coupled to the second expandable cavity, that is configured to:
supply the second fluid to the second expandable cavity to cause the second expandable cavity to expand, or
withdraw the second fluid from the first lumen to enable the second expandable cavity to contract; and
a surgical sheath configured to be received within a tubular structure formed by the second expandable cavity when the second expandable cavity is expanded,
wherein the surgical sheath is configured to form a corridor of access to the region of interest.

41. A surgical procedure associated with accessing a region of interest comprising:
creating an incision in a tissue;
inserting a surgical instrument with a navigation probe in the incision in the tissue,
wherein the surgical instrument comprises:
a multi-lumen catheter that includes:
a first lumen configured to enable a flow of first fluid,
a second lumen configured to receive the navigation probe, and
a first expandable membrane situated to form a first expandable cavity based on the flow of the first fluid, and
a second expandable membrane situated to form a second expandable cavity based on a flow of a second fluid;
locating the region of interest using the navigation probe;
supplying, via a primary fluid line coupled to the first lumen, the first fluid to the first expandable cavity,
wherein the first fluid is supplied to the first expandable cavity to cause the second expandable membrane to apply a relatively uniform force against the tissue of the incision;
supplying, via a second fluid line coupled to the second expandable cavity, the second fluid to the second expandable cavity,
wherein the second fluid is supplied to the second expandable cavity to cause the second expandable membrane to form a tubular structure that provides a flexible barrier between the tissue and the first expandable cavity;

withdrawing the first fluid from the first expandable cavity to reduce friction between the first expandable membrane and the tubular structure formed by the second expandable membrane;

removing the multi-lumen catheter from the tubular structure without removing the second expandable membrane from the incision; and inserting a surgical sheath into the tubular structure to create a corridor of access, through the surgical sheath, to the region of interest.

* * * * *